United States Patent [19]
Ben-Hur et al.

[11] Patent Number: 6,143,287
[45] Date of Patent: Nov. 7, 2000

[54] METHOD AND COMPOSITION FOR HAIR REMOVAL

[75] Inventors: Ehud Ben-Hur; Maria M. Zuk, both of New York, N.Y.; Wai-Shun Chan, Hackensack, N.J.

[73] Assignee: New York Blood Center, Inc., New York, N.Y.

[21] Appl. No.: 08/607,526

[22] Filed: Feb. 27, 1996

[51] Int. Cl.$^7$ .............................. A61K 7/06; A61K 7/155
[52] U.S. Cl. ........................ 424/73; 424/70.1; 424/450; 606/3; 606/9; 606/133
[58] Field of Search .................. 424/73, 450, 70.4, 424/70.5, 70.1; 8/94.16; 606/9, 133, 131, 3

[56] References Cited

U.S. PATENT DOCUMENTS

| | | | |
|---|---|---|---|
| 4,224,179 | 9/1980 | Schneider | 252/316 |
| 4,235,871 | 11/1980 | Papahadjopoulos et al. | 424/19 |
| 4,708,861 | 11/1987 | Popescu et al. | 424/1.1 |
| 4,900,556 | 2/1990 | Wheatley | 424/450 |
| 5,198,470 | 3/1993 | Zysman et al. | 574/785 |
| 5,226,907 | 7/1993 | Tankovich | 606/133 |
| 5,277,913 | 1/1994 | Thompson et al. | 424/450 |
| 5,362,748 | 11/1994 | Schwen et al. | 514/476 |
| 5,425,728 | 6/1995 | Tankovich | 606/9 |
| 5,647,866 | 7/1997 | Zaias et al. | 606/9 |
| 5,669,916 | 9/1997 | Anderson | 606/133 |

OTHER PUBLICATIONS

Li, et al., entitled "The Feasibility Of Targeted Selective Gene Of The Hair Follicle," *Nature Medicine*, vol. 1, No. 7, pp. 705–706 Jul. (1995).

Grossman, et al., entitled "PDT For Hirsutism," *Lasers In Surgery And Medicine*, Supplement 7, p. 44 (1995).

*Primary Examiner*—James M. Spear
*Attorney, Agent, or Firm*—Amster, Rothstein & Ebenstein

[57] ABSTRACT

The present invention provides a method for removing hair from a selected skin area comprising the steps of (a) applying a liposome composition comprising a photosensitizer to the selected skin area so that the composition is introduced into hair follicle ducts of the skin area, wherein the photosensitizer is present in the composition in an amount effective to undergo a reaction and damage the hair follicles upon application to the skin area of light at an appropriate wavelength, energy and duration to penetrate the skin and activate the photosensitizer; (b) removing from the skin area substantially all of the liposome composition which is not introduced into the hair follicle ducts; and (c) applying light to the skin area at an appropriate wavelength, energy and duration to penetrate the skin and cause the photosensitizer to undergo a reaction to damage the hair follicles. The present invention also provides a composition useful for hair removal.

20 Claims, 2 Drawing Sheets

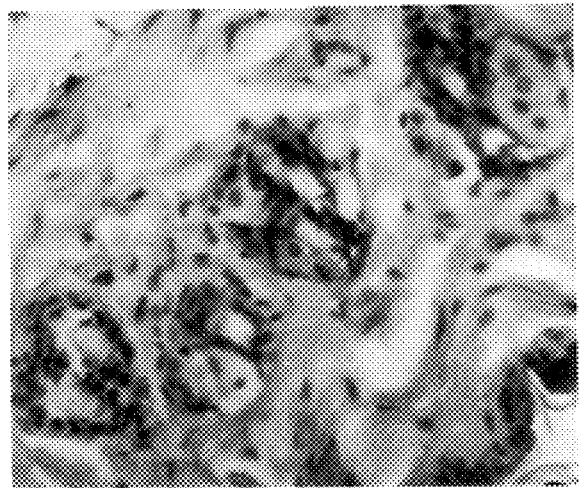
FIG. 1A
FIG. 1B
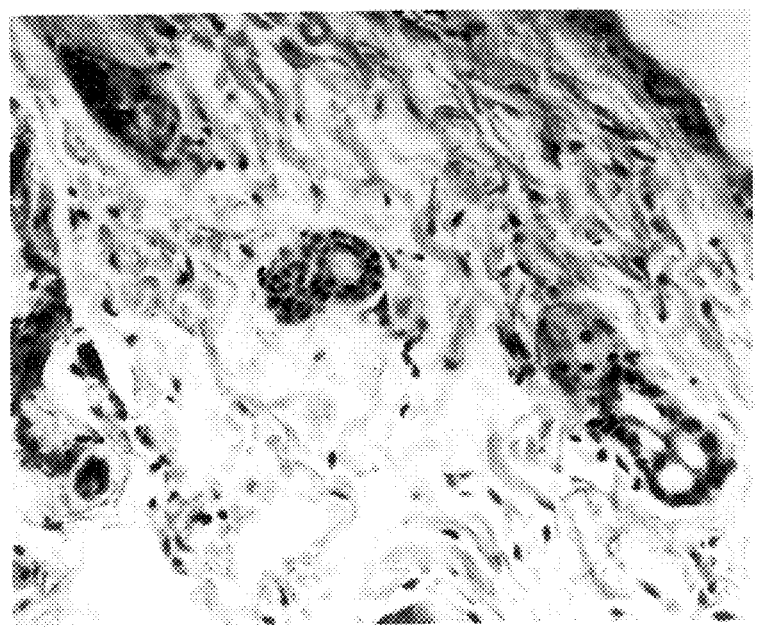
FIG. 1C

METHOD AND COMPOSITION FOR HAIR REMOVAL

BACKGROUND OF THE INVENTION

Currently, the most common methods for hair removal involve the use of hair removal creams, as well as shaving, waxing and electrolysis. Although creams and shaving are popular because they can be readily used at home, they are inadequate because they must be used on a regular basis. Waxing and electrolysis offer longer term hair removal. Both methods, however, can be time-consuming and are often quite painful. For example, removing a typical mustache which contains 1,000 to 2,000 hairs by electrolysis may take up to 50 visits before the hair removal is complete.

More recently, lasers alone or in conjunction with topical formulations containing carbon particles, hair dyes, hematoporphin derivatives or aminolevulinic acid have been used for hair removal (See, U.S. Pat. Nos. 5,226,907 and 5,425,728; Grossman, M. et al. *Lasers Surg. Med. Suppl.* 7:44 (1995)). Such treatments are generally not selective in that they result in only partial destruction of hair follicles and may promote skin reaction.

Accordingly, there exists a need for selectively removing hair that is not time consuming, painful and damaging to the skin, and results in hair removal which is long lasting, and more permanent than conventional hair removal methods. The present invention satisfies this need.

SUMMARY OF THE INVENTION

Accordingly, it is an object of the present invention to provide a method for removing hair that requires little time, is relatively painless and does not damage or irritate the skin.

It also is an object of the present invention to provide a method for removing hair that is long lasting, and more permanent than conventional hair removal methods.

It is a further object of the present invention to provide a liposome composition useful for removing hair.

Additional objects of the present invention will be apparent from the description which follows.

BRIEF DESCRIPTION OF THE DRAWINGS

FIGS. 1A, 1B and 1C provide photographs of the histological sections of skin from mice 3 months after treatment with: 1A) control, no light, no dye; 1B) light exposure of 600–700 nm at 400 J/cm$^2$ 3 hours after application of AlPcS$_{2a}$ liposome formulation; and 1C) light exposure of 600–700 nm at 400 J/cm$^2$ 6 hours after application of AlPcS$_{2a}$ liposome formulation.

DETAILED DESCRIPTION OF THE INVENTION

Figure 2A:
FIGS. 2A, 2B and 2C provide photographs of mice 1 month after treatment with: 2A) control, no light, no dye; 2B) light exposure of 600–700 nm at 100 J/cm$^2$ 30 minutes after application of Pc 4 liposome formulation; and 2C) light exposure of 600–700 nm at 200 J/cm$^2$ 30 minutes after application of Pc 4 liposome formulation.

The present invention provides a method for removing hair from a selected skin area of the body. As used herein "selected skin area" includes any area of the body which contains hair that is desirous of being removed. Such areas include but are not limited to parts of the body to which hair removal is typically desired, such as the face, the female underarms and legs, as well as the hair surrounding the female genital area (i.e. the hair commonly removed in bikini waxes). The method of the present invention also may be used for removing hair from individuals with hirsutism, i.e. excess hair growth over all parts of the body.

In the method of the present invention, a liposome composition comprising a photosensitizer is first applied to the skin area so that the composition is introduced into hair follicle ducts of the skin area. The composition is left on the skin until such time the composition is introduced into the hair follicle ducts, which may vary between about 5 minutes and 6 hours depending upon the choice and concentration of the photosensitizer. The skin area also may be shaved before application of the liposome composition, or left unshaved. Preferably, the skin is shaved before application of the liposome composition.

The liposome composition may be formulated with the photosensitizer by mixing the desired amount of the photosensitizer with the liposome composition. Suitable methods for preparing liposome compositions include but are not limited to the preparations described in U.S. Pat. Nos. 4,224,179, 4,235,871, 4,708,861 and 4,900,566, which are hereby incorporated by reference in their entirety. The liposome composition also may include a pharmaceutically acceptable topical carrier known in the art such as creams, gels, oils and the like.

Suitable photosensitizers include but are not limited to phthalocyanines, porphyrins, purpurins, psoralens, bergaptens, angelicins, chlorins and flavins, which can be activated by light at wavelengths that are sufficient to penetrate into skin to reach the hair follicles (i.e. wavelengths$\geq$500). Particularly preferred photosensitizers are those compounds which absorb in the red region of the visible spectrum such as phthalocyanines. Suitable phthalocyanines include but are not limited to phthalocyanines containing a central atom of aluminum, germanium, gallium, tin or silicon such as silicon phthalocyanine (i.e. hydroxysiloxydimethylpropyl-N-dimethyl silicon phthalocyanine, "Pc 4")), as well as sulfonated or nitrated forms of such pthalocyanines, such as sulfonated aluminum phthalocyanine (i.e. aluminum tetrasulfo-phthalocyanine ("AlPcS$_4$") or aluminum disulfophthalocyanine ("AlPcS$_{2a}$"). Such phthalocyanines and others are described in Spikes, J. *Photochemistry and Photobiology* 43:691–699 (1986); Ben-Hur, E. and Rosenthal, I. *Int. J. Radiat. Biol.* 47:145–147 (1985); Moser, F. H. and Thomas, A. C. *The Phthalocyanines*, Boca Raton, CRC Press, 1984; Kreimer-Birnbaum, M. *Sem. Hematol.* 26:157–193 (1989); and U.S. Pat. Nos. 5,120,649, 5,232,844 and 5,484,778, which are hereby incorporated by reference in their entirety.

The photosensitizer is present in the composition in an amount effective to undergo a reaction and damage or destroy the hair follicles upon application of light to the skin area at an appropriate wavelength, energy and duration to penetrate the skin and activate the photosensitizer. The amount of photosensitizer present in the composition will depend upon the photosensitizer chosen, the duration, wavelength and energy of the light applied. When a phthalocyanine is used, the effective amount of the compound in the composition is preferably between about 50 and about 200 $\mu$g phthalocyanine per ml composition, and more preferably between about 70 and about 140 $\mu$g phthalocyanine per ml composition. Using these concentrations, the effective amount of the phthalocyanine applied is about 5 to about 20 $\mu$g phthalocyanine per cm$^2$ of skin area, and preferably about 7 to about 14 $\mu$g phthalocyanine per cm$^2$ of skin area. However, higher and lower concentrations may be used.

Following application of the liposome composition, it is desirable to remove at least a portion of the composition, and preferably substantially all of the composition, which is present on the skin and which is not introduced into the hair follicle ducts, to prevent any damage or irritation to the skin upon application of the light. As used herein, "substantially all" means the amount of the composition which can be removed from the skin by conventional methods, i.e. by cleaning with an agent such as alcohol, without removing the composition from the hair follicle ducts.

Finally, light is applied to the skin area at an appropriate wavelength, energy and duration to penetrate the skin and cause the photosensitizer to undergo a reaction to damage the hair follicles. Suitable sources of light include commercially available lasers, lamps, light emitting diodes and the like. Preferably, a 500 W xenon short arc lamp, Versa Light, Medic Lightech, Ltd., Haifa, Israel is employed. To achieve the desired wavelength of light, the lamp may be equipped with commercially available filters.

The wavelength of light should be chosen so that it corresponds to or encompasses the absorption of the photosensitizer, and also penetrates deep into the region of the skin encompassing the hair follicles. Photosensitizers absorbing in the red light such as phthalocyanines are preferred since red light is able to penetrate deep into the region of the skin surrounding the hair follicles. The wavelength of light may be a broad range, a narrow range, or a specific wavelength corresponding to the maximum absorption of the photosensitizer used. The energy and duration of treatment will depend upon the wavelength of light applied, as well as the concentration of the photosensitizer in the composition. If a broad wavelength range is chosen, the energy and duration of treatment may be higher and longer, respectively, to achieve the desired effect.

For example, the maximum absorption of phthalocyanines is typically between about 630 nm and about 730 nm. Therefore, in order to activate the phthalocyanine, light may be applied for about 5 minutes to about 6 hours at a broad wavelength range between about 500 nm and about 900 nm, and at an energy between about 200 and about 800 J/cm$^2$ skin area. In another embodiment, light may be applied for about 5 minutes to about 2 hours at a wavelength range between about 600 nm and about 700 nm, and at an energy between about 400 and about 600 J/cm$^2$ skin area. When light is applied at a specific wavelength which corresponds to the maximum absorption of the phthalocyanine or a narrow wavelength range which encompasses the maximum absorption (i.e. the maximum absorption of phthalocyanines is generally between about 630 and about 730 nm), the energy and duration of light applied may be lower (e.g. about 20–90 J/cm$^2$ skin area for about 5 minutes to about 2 hours, or about 40–80 J/cm$^2$ skin area for about 5–45 minutes).

The method of the present invention results in hair removal which is more selective and permanent than conventional hair removal methods. In this regard, the use of the liposome composition permits an appropriate amount of the photosensitizer to be introduced in an efficient manner into all or substantially all of the hair follicle ducts of the skin area to which the composition is applied, as well as deep into the hair follicle ducts. Therefore, upon application of an appropriate wavelength, energy and duration of light, all or substantially all of the hair follicles in the treated skin area, as well as each entire hair follicle or a substantial portion of each hair follicle, can be destroyed. The method of the present invention thus results in the removal of hair which is more permanent than conventional laser/topical formulation hair removal methods which only result in the partial destruction of hair follicles.

The present invention is described in the following Examples, which is set forth to aid in an understanding of the invention, and should not be construed to limit in any way the invention as defined in the claims which follow thereafter.

EXAMPLE 1

Preparation of Phthalocyanines Formulated in Liposomes

A. Sulfonated Aluminum Phthalocyanine (AlPcS$_{2a}$)

This formulation was prepared following a modification of the procedure described in N. Van Rooijen and A. Sanders (*J. Immunol. Methods* 174:83–93 (1994)). A 0.86 ml solution of 100 mg/ml phosphatidylcholine (L-α-lecithin from dried egg yolk) in chloroform was added into a flask containing 8 mg cholesterol in 10 ml chloroform. The chloroform was evaporated under vacuum and then a 3 ml solution containing 4.5 mg AlPcS$_{2a}$ in phosphate buffered saline (PBS) was added. The resulting mixture was shaken vigorously and sonicated briefly and then transferred to a plastic tube and sonicated for 4 min. The suspension was frozen and thawed twice, washed 4 times with PBS by centrifugation and the final pellet was stored until use.

B. Silicon Phthalocyanine (Pc 4)

Pc 4 was dissolved in N-methylpyrrolidone (1 mg in 0.5 ml) prewarmed to 50° C. and sonicated for 2 min. Solutions of 1-palmitoyl-2-oleoylphosphatidylcholine (180 mg/ml) and 1,2-dioleoylphophatidylserine (20 mg/ml) were prepared in t-butyl alcohol prewarmed to 50° C., and combined in equal volumes and kept at 50° C. The Pc 4 solution was mixed with 1 ml of the combined phospholipid solution at 50° C. to obtain a final ratio of Pc4:phospholipids=1:100 (w/w). The 50° C. Pc 4-phospholipid solution was added by dropwise addition to 4° C. excess (×16) aqueous solution of 9.45% D-lactose and 0.027% NaCl, and stirred continuously at 4° C. for 15 min. The resulting liposomal suspension was concentrated (×10) with 100 kDa Amicon concentrator and centrifuged at 3000 rpm at room temperature. The solution was then dialyzed (×3) with a dialysis membrane (Spectrapor 40 mm, MW cutoff at 6000–8000) against lactose-NaCl aqueous solution at 4° C. to remove residues of organic solvents. The solution obtained after dialysis was then lyophilized and stored at 4° C. Prior to use, the liposomal preparation was rehydrated in PBS by vigorous mixing followed by 15 min sonication.

EXAMPLE 2

Photodynamic Treatment (PDT)

Liposomal preparations of either AlPcS$_{2a}$ or Pc 4 were mixed with a water-based cream at a ratio of 1:10. Balb-c mice were shaved and approximately 100 μl of either cream formulation was applied to a circular area (1 cm diameter) at approximately 10 μg dye per cm$^2$. Excess cream was wiped off and the skin was exposed to red light using a 500 W xenon short arc lamp (Versa Light, Medic Lightech Ltd, Haifa, Israel) equipped with filters transmitting light at 600–700 nm via a 1.5 m flexible fiberoptic bundle terminating with a lens. The irradiance at the skin surface was 50 mW/cm$^2$, resulting in no temperature increase during light exposure. Control mice were shaved and received (a) no exposure to red light and liposomal formulation, (b) exposure to red light only or (c) liposomal application with no light. Treated mice were followed up for 3 months, during which time they were photographed for documentation. After 3 months the mice were euthanized and sections of the skin were taken for histology.

Mice treated with 600–700 nm at 400 J/cm² for 1, 3 and 6 hours after application of the AlPcS$_{2a}$ liposome formulation displayed no skin reaction at all times after treatment. When mice were euthanized 3 months after treatment, there was no regrowth of hair on the areas treated with the AlPcS$_{2a}$ liposome formulation and light. In control mice, hair regrew within 1 week in untreated shaved areas. As shown in FIGS. 1B and 1C, histological sections clearly show damaged hair follicles after treatment. This damage was more extensive 6 hours after AlPcS$_{2a}$ application than after 3 hours (compare FIGS. 1B and 1C). Damage was expressed as hypertrophy and closure of the follicles. Even more dramatic was a greatly reduced number of hair follicles per unit area in treated animals. Most of the remaining follicles were in telogen phase (i.e. a phase where hair growth does not occur).

Figure 2B:
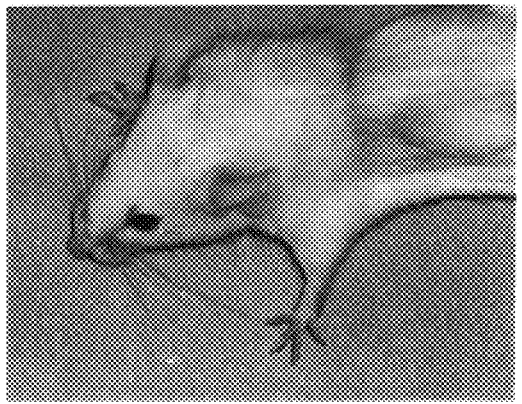
Figure 2C:
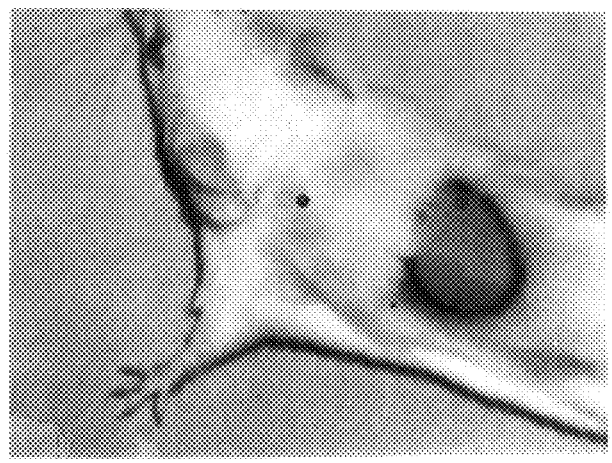

Mice exposed to graded light doses up to 200 J/cm² 30 min after application of Pc 4 liposome formulation displayed no skin reaction after treatment. During the follow-up period control mice regrew their hair within a week. Treated mice displayed a light dose-dependent inhibition of hair growth. Following 200 J/cm² there was no hair regrowth one month after treatment. Mice treated with Pc 4 liposome formulation and light doses up to 100 J/cm² had a reduced rate of hair regrowth (see FIG. 2B).

All publications and patents mentioned hereinabove are hereby incorporated by reference in their entirety.

While the foregoing invention has been described in some detail for purposes of clarity and understanding, it will be appreciated by one skilled in the art from a reading of the disclosure that various changes in form and detail can be made without departing from the true scope of the invention in the appended claims.

What is claimed:

1. A method for removing hair from a selected skin area comprising the steps of:
   (a) applying a liposome composition comprising a phthalocyanine to the selected skin area so that the composition is introduced into hair follicle ducts of the skin area, wherein the phthalocyanine is present in the composition in an amount effective to undergo a reaction and damage the hair follicles upon light activation of the phthalocyanine;
   (b) removing from the skin area substantially all of the liposome composition which is not introduced into the hair follicles; and
   (c) applying light to the skin area at the appropriate wavelength, energy, and duration to penetrate the skin and cause the phthalocyanine to undergo a reaction to damage the hair follicles;
   wherein the light is applied for about 5 minutes to about 6 hours, at a wavelength between about 500 and about 900 nm, and at an energy between about 20 and about 800 J/cm² skin area.

2. The method of claim 1, wherein the phthalocyanine is an aluminum, germanium, gallium, tin, or silicon phthalocyanine; a sulfonated aluminum, germanium, gallium, tin, or silicon phthalocyanine; or a nitrated aluminum, germanium, gallium, tin, or silicon phthalocyanine.

3. The method of claim 2, wherein the phthalocyanine is a sulfonated aluminum phthalocyanine.

4. The method of claim 3, wherein the sulfonated aluminum phthalocyanine is aluminum tetrasulfophthalocyanine or aluminum disulfophthalocyanine.

5. The method of claim 2, wherein the phthalocyanine is a silicon phthalocyanine.

6. The method of claim 5, wherein the silicon phthalocyanine is hydroxysiloxydimethylpropyl-N-dimethyl silicon phthalocyanine.

7. The method of claim 1, wherein the effective amount of phthalocyanine applied is between about 5 and about 20 μg phthalocyanine per cm² skin area.

8. The method of claim 1, wherein the effective amount of phthalocyanine applied is between about 7 and about 14 μg phthalocyanine per cm² skin area.

9. The method of claim 1, wherein the light is applied at a wavelength between about 600 and about 700 nm.

10. The method of claim 1, wherein the light is applied at an energy between about 400 and about 600 J/cm² skin area.

11. The method of claim 1, wherein the light is applied at a wavelength between about 600 and about 700 nm, and at an energy between about 400 and about 600 J/cm² skin area.

12. The method of claim 1, wherein the light is applied for about 5 minutes to about 2 hours, at a specific wavelength corresponding to the maximum absorption of the phthalocyanine, and at an energy between about 20 and about 90 J/cm² skin area.

13. The method of claim 1, wherein the light is applied for about 5 minutes to about 45 minutes at a specific wavelength corresponding to the maximum absorption of the phthalocyanine, and at an energy between about 40 and about 80 J/cm² skin area.

14. A liposome composition comprising a phthalocyanine in an amount effective to undergo a reaction to damage hair follicles upon introduction of the composition into hair follicle ducts and application of light at an appropriate wavelength, energy, and duration to penetrate skin and activate the phthalocyanine, wherein the effective amount of phthalocyanine in the composition is between about 50 and about 200 μg phthalocyanine per ml composition.

15. The composition of claim 14, wherein the effective amount of phthalocyanine in the composition is between about 70 and about 140 μg phthalocyanine per ml composition.

16. The composition of claim 14, wherein the phthalocyanine is an aluminum, germanium, gallium, tin, or silicon phthalocyanine; a sulfonated aluminum, germanium, gallium, tin, or silicon phthalocyanine; or a nitrated aluminum, germanium, gallium, tin, or silicon phthalocyanine.

17. The composition of claim 14, wherein the phthalocyanine is a sulfonated aluminum phthalocyanine.

18. The composition of claim 17, wherein the sulfonated aluminum phthalocyanine is aluminum tetrasulfophthalocyanine or aluminum disulfophthalocyanine.

19. The composition of claim 14, wherein the phthalocyanine is a silicon phthalocyanine.

20. The composition of claim 19, wherein the silicon phthalocyanine is hydroxysiloxydimethylpropyl-N-dimethyl silicon phthalocyanine.

* * * * *